United States Patent [19]
Alphey et al.

[11] Patent Number: 5,376,675
[45] Date of Patent: Dec. 27, 1994

[54] CONTROL OF PARASITIC NEMATODES (A)

[75] Inventors: Thomas J. W. Alphey; Andrew N. E. Birch, both of Dundee, Scotland; Linda E. Fellows, London, England; Walter M. Robertson, Perth, Scotland

[73] Assignee: British Technology Group Limited, London, England

[21] Appl. No.: 70,391

[22] PCT Filed: Nov. 28, 1991

[86] PCT No.: PCT/GB91/02111

§ 371 Date: Aug. 30, 1983

§ 102(e) Date: Aug. 30, 1993

[87] PCT Pub. No.: WO92/09202

PCT Pub. Date: Jun. 11, 1992

[30] Foreign Application Priority Data

Dec. 3, 1990 [GB] United Kingdom ............ 9026271

[51] Int. Cl.$^5$ ............................................ A01N 43/36
[52] U.S. Cl. ............................................. 514/425
[58] Field of Search ................................ 514/425

[56] References Cited

FOREIGN PATENT DOCUMENTS 0322395 6/1989 European Pat. Off. .
1118360 6/1986 Japan ............................. 514/425

OTHER PUBLICATIONS

L. Fellows, "The sugar-shaped weapons of plants", New Scientist, 40 & 41, 15 Aug. 1985.
L. E. Fellows, "The Biological Activity of Parlyhydroxyalkaloids from Plants", pesticide Science 17, 602–606 (1986).
L. E. Fellows et al., "Polyhydroxy Plant Alkaloids as Glycosidase Inhibitors and their possible ecological role", American Chemical Society Symposium Series 296, Publication of symposium held Apr.–May 1985, Miami Beach, Chapter 6, pp. 72–76.
L. E. Fellows & G. W. J. Fleet, "Alkaloidal Gylcosidase Inhibitors from Plants" in Natural Products Isolation, ed. G. H. Wagman and R. Cooper, Elsevier Amsterdam (1988) pp. 540–565.
M. S. J. Simmonds et al. "Wild Plants a Source of Novel Anti–insect Compounds: Alkaloidal Glycosidase Inhibitors", in New Crops for Food and Industry, ed. G. E. Wickens, N. Haq and P. Day, (1989), Chapter 36, pp. 365–378.
L. E. Fellows et al., "Castanospermine, Swainsonine and related polyhydroxy alkaloids: structure, distribution and biological activity", in Plant Nitrogen Metabolism, ed. Jonathan E. Poulton, John T. Romeo and Eric E. Conn, Plenum Publishing Corporation (1989), pp. 395–427.
L. Fellows, "Botany breaks into the candy store", New Scientist, 45–48 (26 Aug. 1989).
M. S. J. Simmonds et al., "Behavioral and Electrophysiological Study of Antifeedant Mechanisms associated with Polyhdyroxy Alkaloids," J. Chemical Ecology 16 (11), 3167–3196 (1990).
D. H. Janzen et al., "What Protects Lonchocarpus (Leguminosae) Seeds in a Costa Rican Dry Forest!", Biotropica 22 (3) 272–285 (1990).
L. Fellows, "Sugar-shaped bullets from plants", Chemistry in Britain, 842–844 (Sep. 1987).
Blaney et al, Entomol. exp. Appl, vol. 36, (1984) pp. 209–216.
Evans et al, Entomol. exp. Appl. vol. 37, (1985) pp. 257–261.

*Primary Examiner*—Richard L. Raymond
*Assistant Examiner*—Mary C. Cebulak
*Attorney, Agent, or Firm*—Nixon & Vanderhye

[57] ABSTRACT

The use of the compound 2R,5R-dihydroxymethyl-3R,4R-dihydroxypyrrolidine (DMDP)

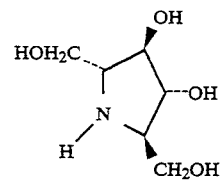

or an acid addition salt thereof in controlling diseases caused by parasitic nematodes in plants or mammals.

3 Claims, No Drawings

CONTROL OF PARASITIC NEMATODES (A)

FIELD OF INVENTION

This invention relates to the control of diseases caused by parasitic nematodes in plants and mammals.

PRIOR ART

Since the early 1940s many chemical compounds active against plant parasitic nematodes have been available. These have often displayed undesirable toxic effects, for example the fumigant dibromochloropropane was withdrawn from the market in 1977, as it was thought to cause sterility in workers. During the 1960's fumigant type nematicides were largely superseded by granular systemic nematicides. These have been in use since then, a representative compound being oxamyl. These compounds are mainly oximecarbamates or organophosphate derivatives, and because of their toxicity have to be used in a strictly controlled manner. Accordingly it would be of benefit to have anti-nematode agents that are environmentally favourable, i.e. being non-toxic themselves and in their degradation products to non-target organisms.

Additional prior art is referred to in a separate section after "Summary of the Invention", without which its context would not be clear.

SUMMARY OF THE INVENTION

The present invention provides the use of the compound 2R,5R-dihydroxymethyl-3R,4R-dihydroxypyrrolidine (DMDP)

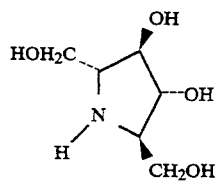

or an acid addition salt thereof, for use in controlling diseases caused by parasitic nematodes in plants, including crops, and in mammals. The invention also includes seeds, dressed, coated or impregnated with DMDP or a said salt thereof.

The mechanism through which DMDP controls diseases caused by parasitic nematodes in plants may include any nematotoxic, nematostatic or anti-feedant effect on either adult or juvenile nematodes, inhibition of hatching of larval forms of nematodes, inhibition of root gall formation by nematode feeding, and further extends to any effect on a nematode that prevents its acquisition and/or transmission of plant viruses.

DMDP is of natural origin and has been shown to display low phytotoxicity.

ADDITIONAL PRIOR ART

The discovery and extraction of DMDP is described by L. E. Fellows and G. W. J. Fleet in "Alkaloid Glycosidase Inhibitors from Plants" (In "Natural Products Isolation", G. H. Wagman and R. Cooper, Eds., Elsevier, Amsterdam, 1988, pp 540–565). In that review certain properties of DMDP, including insecticidal and insect deterrent activity, both as determined experimentally in feeding tests, are referred to. They are more clearly described in L. E. Fellows, Chemistry in Britain pp 842–844 (1987). These and other properties of DMDP are more extensively reviewed in Chapter 11 of "Plant Nitrogen Metabolism", Plenum Publishing Corporation, 1989, pp 395–427, by L. E. Fellows et al., especially at pages 410 (which refers to S. V. Evans et al., Entomol. Exp. Appl. 37, 257–261 (1985), 411 (which refers to the authors' own work and to W. M. Blaney et al., Entomol. Exp. Appl. 36, 209–216 (1984) and 415. See also L. E. Fellows et al., in "Swainsonine and Related Glycosidase Inhibitors", L. James, A. D. Elbein, R. J. Molyneux and C. D. Warren, Eds., Iowa State University Press, 1989, pp 396–416. The properties of DMDP referred to therein are not indicative of an antinematode effect.

DESCRIPTION OF THE PREFERRED EMBODIMENTS

A further advantage of DMDP lies in its mode of application when treating plants, especially crops. Many existing anti-nematode compounds are applied to the soil by broadcasting and incorporated using rotary cultivation. DMDP can be applied to the leaves, which, somehow produces an anti-nematode action in the roots of the plant. Possibly DMDP is translocated through the phloem, but this is not certain. Hence, DMDP may be applied in the form of a foliar spray instead of or in addition to the above-mentioned conventional means of application. A suitable dosage for soil application of DMDP is from at least 24 to at most 48 kg/ha at 20 cm depth. DMDP may also be applied by pre-treating plant seeds before sowing.

DMDP is water-soluble and can therefore be applied without a surfactant or dispersing agent. The preferred concentration of active ingredient and rate of application depend on the mode of application and type of effect desired, e.g. they may differ for nematotoxicity and for inhibition of virus transmission. For foliar spraying it is suggested that normally the plants be sprayed with a solution containing 0.01 to 3–5 g./liter, preferably 0.01 to 1.0 g./liter of the active ingredient, until the spray runs off. Lower concentrations can be more useful in some circumstances, while higher concentrations will often be tolerable.

DMDP displays its properties against a wide range of nematodes affecting plants, e.g. root-knot nematodes, cyst nematodes and virus-transmitting nematodes. Of particular note is its activity against the crop-damaging nematodes of the following genera: Meloidogyne, Globodera, Heterodera, Radopholus, Pratylenchus, Hirschmanniella, Scutellonema, Helicotylenchus, Tylenchus, Rotylenchus, Ditylenchus, Longidorus, Xiphinema. With regard to nematodes which infest mammals, DMDP is active against a wide range of helminthic nematodes, especially those of the following genera: Haemonchus, Teladorsagia, Nematodirus, Trichostrongylus, Dictyocaulus and Cooperia, particularly the species *Haemonchus contortus* and *Teladorsagia circumcincta* (previously classified as *Ostertagia circumcincta*).

DMDP may be extracted from *Derris elliptica* Benth (Leguminosae) as described by A. Welter et al (Phytochem., 1976, 15, 747–749) or may be synthesized from D-glucose (Fuhrman et al., Nature, 1984, 307, 755–758); G. W. J. Fleet and R. W. Smith Tetrahedron Letters 26 (11) 1465–1468 (1985) or from L-sorbose (P. Card et al., J. Org. Chem., 1985, 50, 891–893).

The above description of DHDP applies also to its acid addition salts, which can be any which are compatible with the intended use, e.g. agriculturally or veterinarily acceptable if the use is on plants or non-human animals respectively. Such salts can be made in the conventional way from the free base.

The following Examples illustrate the invention. "Tween" is a Registered Trade Mark. The units "ppm" signify a solution containing mg. of test compound per liter of water, in solutions for in vitro tests or in solutions for application to leaf surfaces. In the Examples, "DMDP" means the free base.

EXAMPLE 1

Virus Acquisition and Transmission Experiments

The effect of a chemical on virus acquisition by a nematode vector was tested by exposing virus-free nematodes to a virus infected source plant in the presence of the test chemical. By comparing subsequent rates of virus transmission between treated and untreated nematodes the efficacy of the chemical can be determined.

Whether a chemical affects the transmission of the virus can be determined by applying the chemical after the nematodes have acquired the virus, at the time they are about to feed on receptor plants.

Experiments were performed in 25 cm$^3$ plastic pots maintained in temperature controlled cabinets (Taylor & Brown, Nematol. medit., 1974, 2, 171-175) using three week old seedlings of Petunia hybrida Vilm. The nematode/virus combination used was Xiphinema diversicaudatum vectoring Arabis Mosaic Virus.

Petunia seedlings were potted in 22 ml of 3:1 sand/loam mixture. Forty-eight hours later the plants were inoculated with virus. After a further 24 hours 5 adult nematodes were added to each pot. (The test chemicals are added at this time if virus acquisition is being tested.) There were 10-15 replicates of each treatment. After 4 weeks the nematodes were extracted, and then added to the soil in which virus-free receptor plants were growing. (If virus transmission is being tested, the test chemicals are added at this time.) After a further 4 weeks the nematodes were again extracted and counted. The galls on the roots of the receptor plants were counted, the roots macerated and the sap applied to the leaves of Chenopodium quinoa plants (virus indicators).

Twelve days later the C. quinoa plants were examined for the symptoms of the virus. There were 10-15 replicates of each treatment in both virus tests. In all cases controls were run in which no chemicals were added.

The chemicals tested were DMDP (15 and 30 ppm) and a conventional nematotoxic compound oxamyl (7 ppm).

Table 1a shows the effect of DMDP inhibiting root gall formation and per cent virus acquisition as compared to the control value.

Table 1b shows the effect of DMDP inhibiting root gall formation and per cent virus transmission as compared to the control value.

TABLE 1a

Feeding and acquisition of Arabis Mosaic Virus by Xiphinema diversicaudatum

| Treatment | Mean No. galls/root | % virus acquisition | No. of Replicates |
|---|---|---|---|
| Control | 1.5 | 33 | 15 |
| DMDP 15 ppm | 0.5 (66%) | 27 (18%) | 15 |
| DMDP 30 ppm | 0.4 (74%) | 7 (79%) | 14 |
| Oxamyl 7 ppm | 0.3 (80%) | 0 (100%) | 10 |

( ) is % reduction in treatment compared to control

TABLE 1b

Feeding and transmission of Arabis Mosaic Virus by Xiphinema diversicaudatum

| Treatment | Mean No. galls/root | % virus transmission | No. of replicates |
|---|---|---|---|
| Control | 1.5 | 64 | 11 |
| DMDP 15 ppm | 0.4 (74%) | 72 (0%)* | 10 |
| DMDP 30 ppm | 0.5 (66%) | 18 (72%) | 11 |
| Oxamyl 7 ppm | 0.7 (53%) | 1 (98%) | 11 |

( ) is % reduction in treatment compared to control
*treatment values higher than control

EXAMPLE 2

Hatch Test

The hatch test examines the effect of the test chemicals on the egg hatch of Globodera pallida, the white Potato Cyst Nematode (PCN).

Ten PCN cysts of uniform size and colour were put in a tube with 0.25 ml of the test compound solution (concs. 50 ppm and 100 ppm) and 0.75 ml of potato root diffusate. Root diffusate normally stimulates the juveniles to hatch from eggs in the cysts. There were 4 replicates of each treatment. Twice each week the liquid was removed and the number of hatched live and dead juveniles counted. The diffusate/chemical mixture was replenished after each nematode count. The tubes were stored at 19° C. between counts.

Table 2a shows the number of hatched juveniles, dead or alive, as the means from four replicates. The same data are also expressed as % effect. This Table shows that DMDP greatly decreases the number of juveniles hatching from cysts.

This experiment was repeated using Globodera rostochiensis. Table 2b shows the % decrease in nematodes alive as compared to the control after 4 weeks. From Table 2b, it can be seen that DMDP provides better effects than its acid salt.

TABLE 2a

Potato Cyst Nematode Hatch Test

| Treatments | Hatched Juveniles | | Total Juveniles |
|---|---|---|---|
| | Live (% increase)* | Dead (% increase)* | Hatched (% decrease)* |
| 15 days exposure | | | |
| Control | 698 | 16 | 714 |
| DMDP 50 ppm | 374 (46) | 68 (325) | 442 (38) |
| DMDP 100 ppm | 203 (71) | 91 (468) | 294 (59) |
| 24 days exposure | | | |
| Control | 1257 | 32 | 1289 |
| DMDP 50 ppm | 1056 (16) | 112 (250) | 1168 (9) |
| DMDP 100 ppm | 601 (52) | 150 (368) | 751 (42) |

TABLE 2b

Globodera rostochiensis cyst Hatch Test

| | Conc (ppm) | | | | | | |
|---|---|---|---|---|---|---|---|
| Test Compound | 220 | 100 | 50 | 25 | 12.5 | 6.25 | 3.12 |
| DMDP | 32 | 38 | 52 | 52 | 41 | 0 | 10 |
| DMDP.HCl | 0 | 0 | 0 | 0 | 27 | 31 | 21 |

*All percentages are based on the control value

EXAMPLE 3

In Vitro Toxicity Test

Groups of ten active adult Xiphinema diversicaudatum were hand-picked into individual watchglasses containing distilled water. At a given time the batches of nematodes were transferred into 1 ml aliquots of test compound, at various concentrations of the test compound, or for the control into 1 ml of distilled water. There were three replicates of each treatment. At two intervals, viz. 48 and to 72 hours, the number of nematodes which were immobilised were recorded. They were considered as immobile if they failed to move when stimulated by prodding with a bristle. All tests were carried out at 5° C.

Table 3a shows the in vitro toxicity of DMDP over a range of concentrations. The percent immobility shown is corrected for control immobilities using Abbott's formula. Note the decrease in in vitro toxicity at 200 ppm and above. There is also an anomalous drop in toxicity at 25 ppm.

In similar tests differences in toxicity to adult and juvenile nematodes were found. Table 3b shows the $EC_{50}$ values (effective concentration required to immobilise 50% of the total number of nematodes) calculated from the results.

This experiment was repeated, replacing *X. diversicaudatum* with *Globodera rostochiensis*. These results are shown in Table 3c, from which it can be seen that both DMDP and its acid salt are toxic to nematodes.

TABLE 3a

In vitro toxicity (adult *Xiphinema diversicaudatum*)

| Test compound | Conc (ppm) | | | | | |
|---|---|---|---|---|---|---|
| | 10 | 25 | 50 | 100 | 200 | 500 |
| | Percent immobility | | | | | |
| DMDP 48 hrs | 15 | 5 | 11 | 35 | 0 | 0 |
| 72 hrs | 39 | 9 | 63 | 78 | 4 | 0 |

TABLE 3b

In vitro toxicity $EC_{50}$ values (ppm) (*Xiphinema diversicaudatum*)

| Test compound | Nematode stage tested | Test duration | |
|---|---|---|---|
| | | 48 hrs | 72 hrs |
| DMDP | Adult | 87.0 | 44.0 |
| DMDP | Juvenile | 94.0 | 0.08 |

TABLE 3c

In vitro toxicity (*Globodera rostochiensis*)

| Test Compound | Conc (ppm) | | | | |
|---|---|---|---|---|---|
| | 2.5 | 10 | 25 | 50 | 100 |
| DMDP | 25 | 37 | 44 | 50 | 37 |
| DMDP.HCl | 88 | 56 | 50 | 50 | 50 |

EXAMPLE 4

Table 4 shows the dose-dependent activity of DMDP, using three tests: the split-pot experiment, the mini-pot experiment and the gall test experiment.

a. Split-pot test

The test shows whether the anti-nematode agents of the invention have a repellent or antifeedant effect on the nematodes and/or a nematicidal effect.

A 'split-pot', i.e. a pot divided into two sections by a fine mesh material (see Alphey et al, Revue Nematol. 1988, 11(4), 399–404), was used. Each side was filled with 37 ml of soil (3:1 sand:loam mixture). Test compounds at the concentrations shown in Table 4 were added to the soil on the side in which a Petunia seedling had been planted. To the other side 100 adult *Xiphinema diversicaudatum* were added. There were 8 replicates of each treatment.

After 21 days the two halves of the pot were separated and the nematodes were extracted from the soil in each half. Root galls were recorded on plants from the treated sides (Table 4a(i)). The numbers of live and dead nematodes from each half were counted and are shown in Table 4a(ii).

Table 4a(i) shows that DMDP has an antifeedant action against nematodes at all concentrations tested. Table 4a(ii) shows that 80 ppm DMDP also possesses a nematotoxic effect in that on the plant side more nematodes were immobilised than in the pot to which oxamyl was applied.

b. Mini-pot test

This test identifies the nematicidal effect of the chemical in soil and its effect on nematode feeding behaviour.

Petunia seedlings were planted in 22 ml of soil (sand:loam—3:1). The test compound solution or water (control) with 5 or 10 adult *Xiphinema diversicaudatum* were added to the soil. There were 10 replicates for each treatment. After 3 weeks the nematodes were extracted and the number of galls induced by nematode feeding on the roots were recorded and expressed as a mean per cent reduction of the control value.

Table 4b shows that DMDP has a nematode repellent or antifeedant action. The most effective rate of DMDP was 25 ppm.

c. Gall test

In the gall test, tomato seedlings, stimulated to produce fine adventitious roots by removing the main root system, were planted in tubes containing 25 g of fine, sieved dry sand, 350 *Meloidogyne incognita* (J2) and DMDP, in solution in water. The effect of DMDP on the ability of the nematodes to gall the plant roots was studied over a 10–12 day period. A water control was included in the test. There were 10 replicates of each treatment.

Table 4c shows the results, from which it will be seen that DMDP is equally effective in the range 2.5–25 ppm but less effective at 50 and 240 ppm. The various tests indicate similar levels of activity of DMDP used between 2.5 ppm and 100 ppm

TABLE 4

4a.(i) Split-pot Experiment (*X. diversicaudatum*/Petunia)

| Chemical/conc (ppm) | Mean reduction galls/root as % of control |
|---|---|
| DMDP/15 | 63 |
| DMDP/30 | 83 |
| DMDP/80 | 89 |

4a.(ii) Mean numbers of nematodes recovered after 21 days in the planted and non-planted sides of the split pot (*X. diversicaudatum*/Petunia)

| Test Chemical | conc (ppm) | Total Nematodes | | Mobile Nematodes | | Immobile Nematodes | |
|---|---|---|---|---|---|---|---|
| | | Plant | No plant | Plant | No plant | Plant | No plant |
| DMDP | 16 | 27 | 15 | 24 | 10 | 3 | 5 |
| DMDP | 32 | 24 | 14 | 21 | 11 | 3 | 3 |
| DMDP | 80 | 25 | 15 | 12 | 11 | 13 | 4 |
| Oxamyl | 15 | 17 | 21 | 13 | 14 | 4 | 7 |
| Control | — | 33 | 16 | 31 | 12 | 2 | 4 |

| 4b. Mini-pot Experiment (*X. diversicaudatum*/Petunia) | | |
|---|---|---|
| | Mean reduction galls/root as % of control | |
| Chemical/conc (ppm) | 5 nematodes/pot | 10 nematodes/pot |
| DMDP/8 | 70 | — |
| DMDP/14 | 70 | — |
| DMDP/25 | 94 | 72 |
| DMDP/50 | 72 | 83 |
| DMDP/100 | 65 | 100 |

| 4c. Gall Test (*M. incognita*/Tomato) | |
|---|---|
| Chemical/conc (ppm) | Reduction in galls/root as % of control |
| DMDP/2.5 | 76 |
| DMDP/12.5 | 70 |
| DMDP/25 | 72 |
| DMDP/50 | 50 |
| DMDP/240 | 47 |

EXAMPLE 5

Mode of Application a) root application

To test whether the anti-nematode agent would be more effective when taken up systemically by plants, the mini-pot test was adapted. The roots of *Petunia hybrida* were removed and the cut ends of the stems from which the newly formed roots were growing were put in a solution of test compound (concentration as shown in Table 5) for 24 hours prior to the start of the experiment. The effects of these treated plants to *X. diversicaudatum* were compared to that of plants whose cut ends had been immersed in water for 24 hours. Table 5 shows that root uptake following soil application is a suitable method of treatment with DMDP.

b) foliar application

The mini-pot test and gall test described in Example 4 were repeated but the test compounds were administered by being painted on to the leaves of the tomato seedlings. In these tests, 0.4 ml test compound in solution in water at 200 ppm, or water alone, together with 0.05% "Tween 80" wetting solution, were painted onto the leaves.

The reductions in galling of 86% in the mini-pot test and 79% in the gall test, over the controls, show that the effect of the test compounds was expressed in the root system to provide protection against nematodes.

TABLE 5

| Activity following uptake through root - details as in text Mini-pot test: Petunia/*Xiphinema diversicaudatum* (21 days) | |
|---|---|
| Chemical/conc (ppm) | % reduction in root galling relative to controls |
| Oxamyl/50 | 92 |
| DMDP/15 | 83 |
| DMDP/30 | 100 |

TABLE 5-continued

| Activity following uptake through root - details as in text Mini-pot test: Petunia/*Xiphinema diversicaudatum* (21 days) | |
|---|---|
| Chemical/conc (ppm) | % reduction in root galling relative to controls |
| DMDP/100 | 58 |

EXAMPLE 6

Phytotoxicity Data

DMDP was tested on three different plant species at 200 ppm for 14 days using methods outlined in the mini-pot test. The seedlings were then left to grow for 16 days and the % growth measured relative to control plants. Root length and shoot length were also measured.

Table 6 shows the effect of DMDP on plant growth. All figures are % growth relative to controls (100%=same as control, >100%=greater than control).

Rye grass when treated with DMDP only grew to 65% of the control weight. This may not be significant in the field as the concentration of DMDP (200 ppm) used was twice its effective dosage required to control nematodes.

TABLE 6

| | Phytotoxicity data (all at 200 ppm soil water) | | | | | | | | |
|---|---|---|---|---|---|---|---|---|---|
| | Root length | | | Shoot length | | | Total weight | | |
| Chemical | TOM | OSR | RG | TOM | OSR | RG | TOM | OSR | RG |
| Oxamyl | 107 | 84 | 108 | 91 | 95 | 93 | 103 | 104 | 107 |
| DMDP | 90 | 98 | 105 | 90 | 97 | 74 | 100 | 100 | 65 |

Plants
TOM = Tomato (cv. Moneymaker)
OSR = Oilseed rape (cv. Bienvenue)
RG = Rye grass (cv. Melle)

EXAMPLE 7

Canister Test

Small 60 ml clear canisters were filled with approximately 25 g soil. 1 ml test compound and 1 ml water containing 1500 PCN eggs was added. Small pieces of Desiree potato with sprout were placed into the compost. Lids pierced 3–4 times were used to close the canisters. The canisters were then put on a tray, covered with black polythene and Kept at a constant 20° C. After 4 weeks the first cyst count was taken, then every following week until the end of the eighth. Table 7 shows the % reduction in cysts, as compared to the control. It can be seen that DMDP was effective in reducing the number of cysts developing.

TABLE 7

| Canister test (*Globodera rostochiensis*) | | | | | | | |
|---|---|---|---|---|---|---|---|
| | % reduction in cysts Conc (ppm) | | | | | | |
| Test Compound | 3.12 | 6.26 | 12.5 | 25 | 50 | 100 | 200 |
| DMDP | 7 | 0 | 14 | 46 | 43 | 35 | 7 |
| DMDP.HCl | 0 | 0 | 0 | 7 | 7 | 43 | 0 |

EXAMPLE 8

Methods of Application II

As an extension to Example 5, further experimentation was undertaken in sand and soil, or a variety of plants and nematodes to demonstrate the different methods of applying DMDP.

8(1) Sand Drench Test in a Tube

Glass tubes (7.5 cm×2.5 cm) were filled with 24.5 g sieved dried sand. 4 ml nanopure water was added and a hole made in the sand. 1 ml test compound and 1 ml water containing 350 *Meloidogyne javanica* were added immediately before a tomato seedling was planted in the hole. All tubes were then left for 14 days. In this experiment and in B(2) below, seedlings were prepared by having their roots cut off and fine adventitious roots allowed to regenerate prior to use. Table 8(1) shows the effect of DMDP and its acid salt over a range of concentrations. Results are shown as % reduction in live nematodes as compared to a control (no test compound).

8(2) Sand Foliar Test in a Tube 3 glass tubes (7.5 cm×2.5 cm) were filled with 24.5 g sieved dried sand. 5 ml nanopure water was added and a tomato seedling planted in the tube. Non-absorbant cotton wool was inserted around the base of the seedling to protect the sand from the test chemical to be sprayed. The tubes were placed in an incubator overnight. Next day, each plant was sprayed with 0.1 ml test chemical from an airbrush and returned to the incubator. On the following day, 1 ml water containing 350 *Meloidogyne javanica* was added to each tube. All tubes were then left for 14 days. Table 8(2) shows the effect of DMDP and its acid salt on a range of plants. Results are shown in % as in Table 8(1).

8(3) Foliar Application 2.5 cm pots were filled with 75 g of Levington universal and sand in a 3:1 ratio. Tomato plants (34 days old) were planted in these pots and 1 ml of water added. The soil was protected with filter paper and the pots left overnight in a glasshouse. Next day, each plant was sprayed with 0.3 ml test compound from an airbrush and then left in the glasshouse Overnight. Next day the filter paper was removed and 350 *Meloidogyne javanica* or *Meloidogyne incognita* in 1 ml water were added to the soil. The pots were then left for 12 days after which the number of live and dead nematodes were counted. Table 8(3) shows the effect of DMDP on a) *Meloidogyne javanica* and b) *Meloidogyne incognita*.

8(4) Soil Application

The procedure of 8(3) was repeated, except that on the first day, 1 ml test compound and 1 ml water with nematodes were added to the soil and the pots left for 14 days. Results are shown in the usual manner in Table 8(4).

TABLE 8(1)

Sand Drench
% reduction in galling by *M. javanica*

| Test Compound | Conc (ppm) | | | | | |
|---|---|---|---|---|---|---|
|  | 200 | 100 | 50 | 25 | 10 | 5 | 1 |
| DMDP.HCl |  | 47 | 51 | 30 | 18 | 43 | 13 |
| DMDP (Expt. 1) | 77 |  | 72 |  | 79 |  | 76 |
| DMDP (Expt. 2) | 56 | 57 | 53 | 56 | 68 | 63 | 71 |

TABLE 8(2)

Sand Foliar
% reduction in galling by *M. javanica*

| Plant | Test Compound | Conc (ppm) | | | | |
|---|---|---|---|---|---|---|
|  |  | 3200 | 2400 | 1600 | 800 | 400 |
| Tomato | DMDP |  |  | 59 | 0 | 9 |
|  | DMDP.HCl |  |  | 18 | 5 | 9 |
| Peppers | DMDP | 7 | 7 | 30 | 0 |  |
|  | DMDP.HCl | 9 | 0 | 7 | 0 |  |
| Aubergines | DMDP | 38 | 43 | 34 | 9 |  |
|  | DMDP.HCl | 44 | 50 | 19 | 19 |  |

TABLE 8(3)

Soil Foliar % reduction in galling by a) *M. javanica* b) *M. incognita*

| Test Compound | Conc | | | | | | | | | |
|---|---|---|---|---|---|---|---|---|---|---|
|  | 1600 | 1000 | 800 | 400 | 200 | 100 | 50 | 25 | 10 | 1 | 0.1 |
| a) DMDP | 27 |  | 27 | 22 | 22 |  |  |  |  |  |  |
| a) DMDP |  |  |  | 35 | 28 | 22 | 39 | 34 |  |  |  |
| b) DMDP |  | 24 |  |  | 24 |  |  |  | 26 | 30 | 31 |
| b) DMDP |  |  |  |  |  |  |  |  | 23 | 22 |  |

TABLE 8(4)

Soil Drench % reduction in galling by a) *M. javanica* b) *M. incognita*

| Test Compound | Conc (ppm) | | | | | |
|---|---|---|---|---|---|---|
|  | 100 | 50 | 20 | 10 | 1.0 | 0.1 | 0.01 |
| DMDP | 28 | 19 | 21 |  |  |  |  |
| DMDP | 28 |  |  | 30 | 29 | 20 | 8 |

We claim:

1. A method of controlling diseases caused by nematodes in plants, which method comprises contacting said nematodes with a nematicidally effective amount of 2R,5R-dihydroxymethyl-3R,4R-dihydroxypyrrolidine (DMDP) of formula:

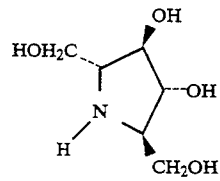

or an acid addition salt thereof in the vicinity of viable plant material.

2. A method according to claim 1, wherein DMDP is applied to the soil.

3. A method according to claim 1, wherein DMDP is sprayed onto the leaves of said plant.